United States Patent
Lewis et al.

(10) Patent No.: US 9,138,242 B2
(45) Date of Patent: Sep. 22, 2015

(54) FEMORAL HIP STEM EXPLANT SYSTEM

(76) Inventors: Randall J. Lewis, Bethesda, MD (US); Christopher G. Sidebotham, Mendham, NJ (US)

( * ) Notice: Subject to any disclaimer, the term of this patent is extended or adjusted under 35 U.S.C. 154(b) by 1062 days.

(21) Appl. No.: 11/800,347

(22) Filed: May 4, 2007

(65) Prior Publication Data

US 2008/0275566 A1 Nov. 6, 2008

(51) Int. Cl.

| | |
|---|---|
| *A61B 17/58* | (2006.01) |
| *A61B 17/72* | (2006.01) |
| *A61B 17/16* | (2006.01) |
| *A61B 17/17* | (2006.01) |

(52) U.S. Cl.
CPC ......... *A61B 17/1637* (2013.01); *A61B 17/1668* (2013.01); *A61B 17/1717* (2013.01)

(58) Field of Classification Search
CPC ............... A61B 17/154; A61B 17/155; A61B 17/1633; A61B 17/164; A61B 17/1668; A61B 17/1717; A61B 17/175
USPC .......... 623/20.34–20.36; 606/79–105.5, 86 R
See application file for complete search history.

(56) References Cited

U.S. PATENT DOCUMENTS

| | | | | |
|---|---|---|---|---|
| 4,257,411 A | * | 3/1981 | Cho .................................. | 606/96 |
| 4,476,861 A | | 10/1984 | Dimakos et al. .............. | 128/303 |
| 4,702,236 A | | 10/1987 | Tarabichy et al. .............. | 128/92 |
| 4,846,161 A | | 7/1989 | Roger ............................. | 128/92 |
| 4,860,735 A | * | 8/1989 | Davey et al. ..................... | 606/80 |
| 4,919,153 A | | 4/1990 | Chin ................................ | 606/93 |
| 4,986,826 A | | 1/1991 | Roger .............................. | 606/82 |
| 5,041,120 A | | 8/1991 | McColl et al. ................... | 606/99 |
| 5,064,426 A | | 11/1991 | Huebsch ......................... | 606/92 |

(Continued)

FOREIGN PATENT DOCUMENTS

| | | | | |
|---|---|---|---|---|
| EP | 0 296 986 | * | 6/1988 | ............. A61B 17/16 |
| EP | 0 552 578 | * | 3/1992 | ................ A61F 2/46 |

OTHER PUBLICATIONS

"A Device for Removal of Femoral Distal Cement Plug During Hip Revision Artroplasty: A High-Powered Drill Equipped with a Centralizer" Jingushi et al., The Journal of Anthroplasty, vol. 15, Iss. 2, Feb. 2000, pp. 231-233, found at: http://www.sciencedirect.com/science?_ob=AritcleURL&_udi=B6WHB-4DJ43B2-K&_coverDate=02%2F29%F2000&_alid=449663217&_rdoc=1&_fmt=&_orig=search&_q d=1&_cdi=6846&_sort=d&view=c&_acct=C000050221&_version=1&_urlVersion=0&_us erid=10&md5=f3479e310a89d34ab521ff1cfcf575d5.

(Continued)

*Primary Examiner* — Matthew Lawson
(74) *Attorney, Agent, or Firm* — Ernest D. Buff & Assoc. LLC; Ernest D. Buff; Margaret A. LaCroirt

(57) ABSTRACT

A femoral hip stem explant system has an alignment body which is attached to two locations of a femoral bone and has several lockable collet type adjustment features to set the shaft of a reamer or end mill exactly in coincidence with the femoral bone cavity axis. The shaft of the end mill or reamer is supported by a sleeve member, which is inserted into a drill guide central aperture. The drill guide aperture is adjusted first and locked to be in line with the femoral bone cavity. Each of the sleeve members has the same mating outer diameter, which fits into the drill guide central aperture. Accordingly, the sleeve members can be interchanged into the drill guide aperture with shafts of differently sized reamers or end mills.

12 Claims, 9 Drawing Sheets

(56) References Cited

U.S. PATENT DOCUMENTS

| | | | | |
|---|---|---|---|---|
| 5,152,792 | A | | 10/1992 | Watkins .................. 623/16 |
| 5,167,619 | A | | 12/1992 | Wuchinich .................. 604/22 |
| 5,190,551 | A | | 3/1993 | Chin et al. .................. 606/99 |
| 5,222,957 | A | | 6/1993 | McColl et al. .................. 606/86 |
| 5,350,380 | A | * | 9/1994 | Goble et al. .................. 606/80 |
| 5,354,300 | A | * | 10/1994 | Goble et al. .................. 606/80 |
| 5,413,578 | A | | 5/1995 | Zahedi .................. 606/86 |
| 5,470,336 | A | | 11/1995 | Ling et al. .................. 606/105 |
| 5,628,750 | A | * | 5/1997 | Whitlock et al. .................. 606/88 |
| 5,649,930 | A | * | 7/1997 | Kertzner .................. 606/96 |
| 5,704,941 | A | * | 1/1998 | Jacober et al. .................. 606/88 |
| 5,833,691 | A | * | 11/1998 | Bimman .................. 606/80 |
| 5,888,034 | A | * | 3/1999 | Greenberg .................. 408/115 R |
| 5,919,195 | A | * | 7/1999 | Wilson et al. .................. 606/80 |
| 6,129,729 | A | * | 10/2000 | Snyder .................. 606/916 |
| 6,190,392 | B1 | | 2/2001 | Vandewalle et al. .................. 606/99 |
| 6,250,858 | B1 | * | 6/2001 | Salyer .................. 408/239 R |
| 6,267,762 | B1 | * | 7/2001 | Millard et al. .................. 606/54 |
| 6,270,502 | B1 | | 8/2001 | Stulberg .................. 606/86 |
| 6,514,253 | B1 | * | 2/2003 | Yao .................. 606/53 |
| 7,037,310 | B2 | * | 5/2006 | Murphy .................. 606/91 |
| 7,104,998 | B2 | * | 9/2006 | Yoon et al. .................. 606/89 |
| 2005/0049601 | A1 | * | 3/2005 | Keller .................. 606/81 |
| 2006/0085010 | A1 | * | 4/2006 | Lieberman .................. 606/99 |
| 2007/0239167 | A1 | * | 10/2007 | Pinczewski et al. .................. 606/87 |

OTHER PUBLICATIONS

"Controlled Perforation. A safe method of cement removal from the Femoral Canal" Sydney et al., Clin. Orthop. Relat. Res., 253, Apr. 1990, pp. 168-172, found at: http://www.ncbi.nlm.nih.gov/entrez/query.fcgi?db=pubmed&cmd=Retrieve&dopt=AbstractPlus&list_uids=2317970&query_h1=2&itool=pubmed_docsum.

"Segmental Cement Extraction at Revision Total Hip Arthroplasty" Schurman et al., Clin. Orthop. Relat. Res., 285, Dec. 1992, pp. 158-163, found at: http://www.ncbi.nlm.nih.gov/entrez/query.fcgi?db=pubmed&cmd=Retrieve&dopt=AbstractPlus&list_uids=1446433&query_h1=w&itool=pubmed_docsum.

\* cited by examiner

General Dimensions

End Mill Cutters
5 mm
6 mm
7 mm
8 mm
9 mm

10" (254 mm) Functional Length

Row Reamers  All cutters will be designed and manufacturesd
10 mm                 with the intent to make them disposable
12 mm
14 mm
16 mm
15 mm Functional Length 10" (254 mm)
Bullet Nose Tip Diameter same as previous reamer Sleeves
5 mm
6 mm
7 mm
8 mm
9 mm
10 mm
12 mm
14 mm
16 mm
18 mm Common shoulder All Sleeves Specific cone sizes for each sleeve size.

FEMORAL HIP STEM EXPLANT SYSTEM

BACKGROUND OF THE INVENTION

1. Field of the Invention

The present invention relates to hip replacement systems; and, more particularly, to a femoral hip stem explant system for the removal of remnant cement mantle following the removal of a femoral prosthesis.

2. Description of the Prior Art

Many patents address issues related to removal of a cement mantle incorporated in the bone cavity, typically used to attach a femoral implant. The femoral implant must be extracted and replaced with a new implant when the implant sockets have worn out or due to poor bond formation. The prosthesis is easily extracted by the application of pressure, but the bone cement mantle used during the implant procedure remains attached to the bone cavity and must be removed by drilling, dissolution or other means. Most commonly used methods include free hand drilling wherein the surgeon uses a drill to approximate the location of the bone cement mantle and significant damage may occur to the bone canal including bone fracture which precludes the possibility of a new implant. In some cases the surgeons use an x-ray fluoroscope to get an outline of the bone cavity and the drill, to manually guide the drill within the bone cavity when drilling out bone cement mantle. Drilling of a hardened bone cement mantle can result in heat generation that may damage bone tissue adjacent to the mantle. This damage may prevent bond formation between the femoral bone and the newly implanted femoral implant. It is therefore necessary to limit the amount of heat generated during this bone cement mantle removal procedure. Methods of bone cement mantle removal disclosed in prior art patents generally comprise (i) sawing, to cuts along the side of the mantle; grinding, using a tracing grinding element, the path of which tracks a template; (iii) casting, to cast a resin inside the bone cavity; and (iv) pulling on the resin, to forcefully remove the bone cement mantle. In lieu of pulling on the resin, there is used a fixture that is attached to the femoral bone by interference. This fixture carries a drill that is translated to drill out the bone cement mantle.

U.S. Pat. No. 4,476,861 to Dimakos et al. discloses an instrument for removal of a hollow bone cement tube from an artificial femur head reimplantation. This instrument has an elongate hollow tube adapted to be inserted into the bone cement tube. The end of the hollow tube within the bone canal has a collet comprising a slot. The slot is expanded by a central mandrel rod so that the collect engages the end of the bone cement tube. A cylindrical striker sliding on the hollow tube applies pressure to the bone cement tube enabling its extraction. For this device to work, a free end that is essentially flat must be available within the bone cement tube so that the collet may be engaged for extraction. This feature is oftentimes unavailable. Moreover, a large amount of force must be applied to release and displace the bone cement tube, which may not be available by the simple back and forth movement of the cylindrical striker.

U.S. Pat. No. 4,702,236 to Tarabichy et al. discloses a revision arthroplasty method and related instrument. This method is for revision arthroplasty or the removal of a loosened or defective prosthesis component set in a bone cavity using polymer cement. The loosened or defective prosthesis is then removed out of the bone cavity. Cement is then removed from the cavity by the use of an instrument having a heated working end. Heating the working end to a temperature exceeding the melting point of the cement enables cement to be removed without perforating or damaging the bone. Such heat in the range of 150° C.-200° C. provides an invasive procedure, and can be damaging to bone tissue, preventing bond formation of an implanted prosthesis.

U.S. Pat. Nos. 4,846,161 and 4,986,826 to Roger disclose a method and apparatus for removing prosthetic cement. This method and device is for use in removing the prosthetic cement from a bone in which an artificial joint, such as hip joint, is to be replaced. The device cuts the prosthetic cement in a longitudinal plane of the prosthetic cavity to the complete depth of the cement, without substantially cutting into the bone. The device includes a reciprocating saw head, which is advanced longitudinally of the cavity and is maintained within the preselected longitudinal plane of the cavity by a guide while it cuts through the cement. The saw head is transversly biased towards the cement, so that it cuts only to a depth defined by the profile of a template. The profile of the template is obtained from X-ray information obtained before commencement of the operation. This reciprocating cutting action only produces a cut in the longitudinal plane of the prosthetic cement. Such a cut does not guarantee easy removal of the prosthetic cement, since the cement is shown to be three dimensional in structure matching the shape of the template. Cutting debris is left behind within the bone cavity, and excessive heating is generated by the cutting action, damaging bone tissue. Multiple cuts are needed to effect any removal of the prosthetic cement. The bottom plug of the prosthetic cement is said to be removed by this removal procedure. However, the saw does not reach the very bottom of the cavity. Consequently, these multiple sections are still held together by the bottom uncut portion, making the removal of the prosthetic cement difficult.

U.S. Pat. No. 4,860,735 to Davey et al. discloses a drill alignment guide for osteoplastic surgery. This drill alignment apparatus for osteoplastic surgery comprises an alignment rod mounted on one or two spaced clamp elements. The alignment rod is parallel to and is disposed at a predetermined distance from a shaft of the drill. The clamp element includes an aperture, which permits passage of the rod. The clamp element is adapted to be affixed to a bone, such as a femur, by interference. With this arrangement, the aperture is displaced from the central axis of the bone by substantially the same distance that the center axis of the alignment rod is displaced from the center axis of the drill shaft. When drilling is commenced, the forward end of the alignment rod is placed within the aperture of the clamp element. As drilling progresses, the rod passes through the aperture, thereby ensuring that drilling occurs along a predetermined drilling path extending along the bone axis. The clamping elements merely rest on the femoral bone with no bottom support. Accordingly, they are subject to lifting, especially when a drilling load is applied. When two clamping elements are used, the parallelism of the alignment rod with respect to the bone cavity is not possible, since the shape of the femoral bone is not exactly cylindrical. An alignment rod support is used to attach the drill to the alignment rod. Thus supported, the alignment rod progressively passes through the aperture in one or two clamp elements as the drill enters through the intramedullary bone canal. However, vertical displacement of the clamp element without any bottom support can cause drilling in a path that is not concentric with the intramedullary bone canal.

U.S. Pat. No. 4,919,153 to Chin discloses a method and apparatus for removing pre-placed prosthetic joints and preparing for their replacement. This method and apparatus removes a pre-placed prosthetic joint from a bone cavity and conditions the cavity for receipt of a replacement joint. The pre-placed joint is first pulled from the mantle of hardened methylmethacrylate cement holding it within the cavity, thus leaving a cavity within the mantle. A mass of fluid methylmethacrylate cement is then placed within the cement cavity. A pulling appliance is inserted into the fluid cement and the fluid cement is permitted to cure to bond the appliance to the mantle. Tension is then applied to the pulling appliance to remove the appliance and the cement mantle from the bone cavity as a unit. The fluid cement partially dissolves and softens the hardened cement mantle so that an integral cement mass is formed upon curing of the fluid cement. The pulling appliance is of a screw-like configuration, with means to connect a slap-hammer to its proximal end. The curing of the fluid methylmethacrylate occurs by exothermic reaction of liquid methyl methacrylate monomer with a finely divided powder mixture of polymethyl methacrylate, methyl methacrylate-styrene-copolymer. This exothermic reaction results in large heat generation, damaging bone tissue and resulting in poor bonding of the new implant. The removal of the bone cement mantle within the cavity by this pulling method requires the cavity to be uniformly tapered outward with the progressively larger dimension towards the bone canal opening. This may not be the case in all intramedullary bone canals since the femoral implant is forced into the canal with the bone cement.

U.S. Pat. No. 5,041,120 to McColl et al. discloses a multipart kit and method of using the same to remove cement used to secure prosthetic joints. A mantle of cement within a bone elongate cavity is removed from the adhered condition by successively breaking away sections of the mantle with a plurality of elongate screw threaded pulling elements proportioned to engage a limited length of a screw threaded mass of cement within the cavity. The apparatus is provided in a kit form having a sufficient number of elements to enable the full length of the mantle to be removed in successive steps. The kit may also include a cement injection syringe and vent tube to fill the cavity of the mantle with a mass of cement, a die to form a screw threaded passage in the mass of cement, and a slap hammer connectable to the pulling elements. This method of removal requires direct attachment by screw thread to a portion of the remaining mantle of cement or attachment of a threaded pulling element by fresh methylmethacrylate cement, which is said to soften the old mantle of cement. Such softening prevents bond creation between the old cement mantle and the freshly applied methylmethacrylate preventing any removal of the old cement mantle. Moreover, methylmethacrylate is a brittle resin and will readily fracture upon being subjected to tensile pull by slap hammer.

U.S. Pat. No. 5,064,426 to Huebsch discloses an apparatus for removal of bone cement. Bone cement is removed from a bone cavity, such as the intramedullary canal, during a prosthetic revision. The bone cement is pre-molded by a thermal chisel, which includes a shaft for extending into the bone cavity, a plasticizer chisel on a working end of the shaft, and a heat element carried by the shaft for heating the chisel to a temperature within a range of temperatures sufficient to plasticize the bone cement. This deforms and weakens the bone cement upon direct non-impact type contact between the heated tip of the chisel and the cement. The cement is removed by pre-molding it with the heated working end of the thermal chisel, preferably by molding a distally located circumferential furrow in the bone cement and then molding circumferentially spaced apart longitudinal furrows from the circumferential groove to the proximal end of the bone cement. Upon rehardening of the bone cement, these thermally molded furrows form weakened areas within the bone cement so that the regions of bone cement between the weakened areas can be removed by an impact type chisel. Use of this heated tip raises the temperature of the cement sufficiently to melt or soften the cement. The bone tissue that is in direct contact with the cement also reaches the same softening or melting temperature, which is a fixed temperature according to the composition of the cement used. Exposure of the bone tissue to such high temperatures compromises the ability of the bone tissue to heal and bond to a new implanted femoral prosthesis.

U.S. Pat. No. 5,152,792 to Watkins et al. discloses an apparatus and method for gauging and controlling process steps used to remove prosthetic joints. Over tightening of the threaded rods used to engage and remove the cement for prosthetic joints is avoided by measuring the depth of the passages into which the rods are threaded. Sleeves on the rods are provided to serve as visual indicia of the extent of penetration of the rods into the cement. A depth gauge is calibrated in both units of length and screw thread turns, for the measuring function. The sleeves are slidably received on the rods and proportioned to engage the edges of the passages into which the rods are threaded. In use, the sleeves slide toward a marker as the rods are threaded into place. Sequentially sized tools are screwed into the mass of cement injected into the bone cement mantle and torsional and pulling force is applied to extract the bone cement mantle. Insertion and hardening of the cement into the bone cement mantle takes time, and the fluid cement injected is said to soften or partially dissolve the bone cement mantle. As a result, the bond between the poured cement and the bone cement mantle is weak and the application of torsional and pulling forces may separate at this interface between the injected cement and the bone mantle cement, resulting in incomplete or poor extraction of the bone cement mantle.

U.S. Pat. No. 5,167,619 to Wuchinich discloses an apparatus and method for removal of cement from bone cavities. This surgical apparatus has a hand piece with a vibration source for generating mechanical vibrations in response to current supplied to the vibrator. A elongated hollow tool is attached to the vibration source of the hand piece. The tool extends away from the hand piece to the cement to be removed. Cement is removed using the surgical apparatus by applying the tool to the cement and thereby applying mechanical vibration to the cement, causing the cement to melt. Removal of cement is accomplished by suction through the hollow elongated tool. In an alternate method, the tool is rotated to apply shear forces to the cement being removed. The tool is then cooled, used to damp lateral vibrations at the tool end. The cement is irrigated, while being melted and removed. In this arrangement, the vibratory and rotary motion of the tool creates sufficient friction generated heat to melt the bone cement mantle, causing molten cement to be drawn through the central aperture of the hollow tube. Since the bone cement mantle is in intimate contact with the bone tissue, such heat generation exposes the bone tissue to heat, preventing its ability to heal and bond to a new implant.

U.S. Pat. No. 5,190,551 to Chin et al. discloses a controlled apparatus and method for extracting cement mantles from bone recesses. A cement plug, received within a bone recess, is extracted by forming a bore within the plug, tapping the bore to form internal screw threads therein, engaging the threads with a pulling tool, and applying tension to the tool to extract the plug. The method for removing a cement mantle includes steps of: (i) filling the bone cavity with a fluid cement; (ii) inserting an elongate curvilinear rod in the fluid cement; (iii) curing the fluid cement, rod, and mantle to form a unitary mass; (iv) withdrawing the curvilinear rod from the mass; (v) tapping to form a screw-threaded section therein; (vi) engaging the screw-threaded section of the bore with a pulling tool; and (vii) imparting pulling force to the pulling tool to remove that portion of the mass within which the tool is thread-ably engaged from the recess. The curing of the fluid cement takes time, which is not generally available in a surgical situation. For this technique to work, the fluid cement must form an intimate bond with the bone cement mantle. Otherwise, the pulled rod, together with the hardened fluid cement, extracts without pulling the bone cement mantle from the bone cavity.

U.S. Pat. No. 5,222,957 to McColl et al. discloses a method and apparatus for extracting a cement mantle from a bone recess. This method and apparatus effects removal of a preplaced prosthetic appliance, anchored in place in a bone recess by a cement mantle, and conditions the recess for receipt of a replacement appliance. The preplaced appliance is first pulled from the mantle of hardened cement, holding it within the recess, thus leaving a cavity within the mantle. A screw threaded post having nuts threadably engaged therewith at longitudinally spaced locations is then anchored within the cavity with a new mass of cement. Thereafter, the post is threadably disengaged from the nuts, leaving the nuts in place within the new mass of cement. A pulling tool is then successively engaged with the nuts and tensioned to incrementally remove the mantle from the recess. The hardening of the new mass cement within bone cement mantle requires time, which is not generally available during surgical procedure. In order to harden a new mass of cement incrementally in one-half inch increments, the bone cement mantle must intimately bond with the old bone cement mantle, and the hardened new mass of cement must fracture at specified incremental locations. In practice, these features may not readily occur, leaving portions of the bone cement mantle within the bone cavity.

U.S. Pat. No. 5,413,578 to Zahedi discloses a device for removing a bone cement tube. This device for removing a bone cement tube in a bone cavity after the removal of the endoprosthesis comprises an ultrasonic generator with an essentially cylindrical guide section, the free end of which carries the sonotrode, which emits the ultrasound. The diameter of the guide section is less than the internal diameter of the bone cement tube, and its length is adapted to the length of the prosthesis shaft or to the length of the bone cement tube. It has been found that a layer of cement, which covers a bone substance, loosens when it is ultrasonically radiated with a frequency in the region of 40 kHz. This cement layer can be removed from the surface of the bone as a complete block of cement. The substance of the bone is not weakened due to this procedure. Since the ultrasonic frequency is emitted by the sonotube, an ultrasonic coupling agent must be disposed between the sonotube and the bone cement tube in order to couple the ultrasonic frequency energy. No such coupling agent is indicated, with the result that energy transfer to the bone cement tube will be inefficient.

U.S. Pat. No. 5,470,336 to Ling et al. discloses a system for performing hip prosthesis revision surgery. This hip prosthesis revision surgery apparatus includes means for preparation of the cavity left after removal of the original prosthesis. The old bone cement tube or mantle is completely removed first by drilling and by progressively increased sizes of reamers. The old restrictor at the bottom of the bone cavity is also removed. The reamed bone cavity is larger in size than that needed for the new implant, and is shaped to proper size by tamping cancellous bone graft material. Following removal of the old prosthesis, old cement and old restrictor, a new cement restrictor or plug is placed at or near the bottom of the cavity in femur. A guide-wire, having external threads, is threadedly engaged with the new restrictor. A tamp having a stem portion and a longitudinal passageway is inserted into the cavity. The tamp is positioned to be driven into the cavity by means of the rasp handle, which is impacted by a hammer or other impacting device as it is driven to the desired position within the cavity to crush the cancellous bone graft to a desired density. Following tamping of the cancellous bone graft material to the desired density and the resultant formation of a cavity having the proper size and shape, the tamp may be removed from the newly formed cavity. The rasp handle is then removed and the guide-wire may be unscrewed and removed from the restrictor. The new cavity is now ready to receive the new prosthesis. The '336 patent disclosure deals with packing a larger sized bone cavity with graft material. It does not address removal of old bone cement mantle that is present when a damaged or worn out femoral implant is removed.

U.S. Pat. No. 5,649,930 to Kertzner discloses an orthopedic centering tool. This centering tool is guides a surgical drill bit through the center of a target obstruction within a bone. An adjustable frame of the centering tool includes a pair of right angle sections mounted in a mirror image relationship. The sections are adjustably clamped to one another and, in turn, secure a vertical sleeve for guiding a surgical drill bit and a horizontal sleeve for accommodating an anchor pin within a coplanar arrangement. Various clamps associated with the frame elements and the sleeves permit a surgeon to adjust the tool so that the drill bit is guided through the vertical sleeve to the approximate center of the bone immediately below the obstruction, while the pin anchors the frame to the bone. The surgical frame is attached to the femoral bone in one location only and the frame is therefore rotatable around this femoral bone attachment point, especially when drilling loads are applied to the vertical sleeve. Any such rotation will lead to meandering of the drill bit within the bone cavity that is being drilled to remove bone cement mantle, causing permanent damage to the bone tissue.

U.S. Pat. No. 6,190,392 to Vandewalle et al. discloses a method and apparatus for ultrasonic removal of bone cement material. Ultrasonic removal of bone cement material is accomplished using an auger tool and an ultrasonic transducer/hand piece. The auger tool includes a spiral helical flute, which extends about a cylindrical body. A quick connect mechanism couples the auger tool to the ultrasonic transducer/hand piece. Upon energizing the hand piece, bone cement is heated to a flowing mass so that the flowing mass of bone cement may flow about the cylindrical body and be guided via the spiral helical flute. Removal of bone cement material is accomplished easily and quickly during a revision type orthopedic surgical procedure. The auger tool is vibrated with sufficient ultrasonic power to cause the bone cement to melt, and the molten cement is guided along the helical flute path. The bone tissue directly below the molten bone cement mantle reaches the melting point of the bone cement. Consequently, the heating temperature employed by the method and apparatus of the '392 patent is oftentimes sufficient to damage bone tissue.

U.S. Pat. No. 6,270,502 to Stulberg discloses methods and instruments for performing radial impacting. This radial impacting technique involves using a set of progressively larger radial impactors to pack a medullary canal in a radial direction toward the cortex. For revision cases, graft material, which may be either synthetic or bone graft material, is added into the medullary canal after the previously installed implant has been removed. Packing the medullary canal in the radial direction, as opposed to the conventional approach of packing in a distal direction, is said to provide superior results. The radial impactors are preferably cannulated and may also have holes to assist in the removal of fluids from within the medullary canal. The profile impactors may be either cannulated or non-cannulated and prepare the medullary canal for receipt of the implant. The '502 patent disclosure deals with packing a bone cavity with graft material. It does not disclose or suggest removing old bone cement mantle that is present when a damaged or worn out femoral implant is removed.

"Controlled Perforation: A Safe Method of Cement Removal from the Femoral Canal", Sydney et al., Clin. Orthop. Relat. Res., 253, April 1990, pp 168-172 discloses a method for removal of cement from a femoral canal. This method involves removal of cement from the canal by way of placing multiple 9-mm perforations at least 5 cm apart on the anterior surface of the femoral shaft. According to the disclosure, the tip of the revision stem should be at least 5 cm distal to the most distal perforation. From January 1984 to December 1986, there were 219 cases of revision total hip arthroplasties performed using this technique. The incidence of ipsilateral postoperative femoral fractures was nine out of 219. Eight of these fractures were at the tip or distal to the femoral prosthesis and were associated with trauma. One fracture occurred through a perforation site and had an associated fracture of the femoral component. Accordingly, this method of drilling multiple 9 mm perforations disclosed by the Sydney et al. publication results in an unreliable surgical procedure.

"A Device for Removal of Femoral Distal Cement Plug During Hip Revision Arthroplasty: A High-Powered Drill Equipped with a Centralizer", Jingushi et al., The Journal of Anthroplasty, Vol. 15, Iss. 2, February 2000, pp 231-233 discloses removal of a femoral cement mantle in hip revision arthroplasty by way of a high-powered drill. The high-powered drill is equipped with a centralizer developed to remove the distal cement plug safely. Using the drill equipped with a centralizer the cement plug is removed well enough to insert a new component without causing perforation during the operation. The bone cement mantle in the bone cavity is not indicated to be removed by the centralizer mounted high powered drill. Only the bottom cement plug is said to be safely removed.

"Segmental Cement Extraction at Revision Total Hip Arthroplasty", Schurman et al., Clin. Orthop. Relat. Res., 285, December 1992, pp 158-163 discloses a method for segmented cement extraction during revision surgery. This technique permits segmental extraction of bone cement from the femoral canal through the introduction of fresh cement into the old cement mantle and placement of a threaded rod into the wet cement. The threaded rod is held in place while the cement hardens. The thread-forming rod is then removed leaving a threaded channel in the cement. Extraction rods are then screwed 1.5 to 2.5 cm into the threaded channel. A slap hammer, which attaches to the opposite end of the extraction rod, is used to remove 1.5- to 2.5-cm segments of cement. Fifteen cases involving revision of cemented femoral components were analyzed using the 'Segmental Cement Extraction reference system. Complete cement removal was achieved in 12 cases. The method produced less damage to the femur when compared with conventional methods. In two cases, there was retained cement along the medial wall of the femur and, in one case, the plug could not be extracted using the 'Segmental Cement Extraction reference's method. This method requires the fresh cement to bond to bone cement mantle. It requires the fresh cement to break at screw insertion depth, and to carry with it a portion of the bone cement mantle. If the bond between the bone cement mantle and the fresh cement is weak, the bone cement mantle is not extracted. If the fresh cement cures to a stronger cement, fracture may occur unpredictably, creating bone cement extraction problems.

There remains a need in the art for a femoral hip stem explant system that reliably and safely removes any remaining bone cement mantle and bottom plug without damaging the bone tissue due to poor drill or reamer placement or subjecting the bone tissue to excessive heat. Also needed is a femoral hip stem explant system that removes all residue of the bone cement within a reasonable time period, so that the operating time is not excessively prolonged.

SUMMARY OF THE INVENTION

The femoral hip stem explant system for removing bone cement mantle from an existing bone cavity. A set of reamers, end mills, sleeve members and an alignment body are adjusted to provide supporting arrangement. The adjustment is such that the reamers, end mills, sleeve members and alignment body line up precisely and reliably with the existing bone cavity from which a bone cement mantle is to be removed.

The alignment body comprises two bone saddles, a tie rod with a central bore and a drill guide body and set of sleeves that support the shaft of the reamers or end mills. The two bone saddles are removably affixed to the femoral bone using two disposable polymeric ties that are inserted behind the femoral bone using a special tool, preventing any movement. The bone saddles are spaced apart from each other and the bottom portion of the bone saddle contacts the femoral bone. This bone contacting portion of the bone saddle has a semi-cylindrical shape with serrations to increase friction against the bone. The disposable plastic tie surrounds the femoral bone and passes through a channel in the bone saddle, firmly anchoring the bottom portion of the bone saddle against the femoral bone. The distal portion of the bone saddle from the femoral bone has a rod portion which mates with a collet terminated support member having a circular aperture. With this arrangement, the length of the bone saddle between its bone resting location and the centerline of the circular aperture may be increased or decreased by loosening the collet and locking it at a new position.

After affixing the two bone saddles on the femoral bone, a tie rod with a central bore is inserted through the circular apertures of the two bone saddles. The fit between the outer diameter of the tie rod and circular aperture of the bond saddle is a snug fit assuring a reliable location and orientation of the tie rod when the collets of the bone saddles are locked.

A drill guide body, which has a central rod and a perpendicular end projection is inserted into the central bore of the tie rod. The insertion depth of the drill guide body, as well as its angular orientation relative to the plane formed by the tie rod and bone saddles, may be changed and locked. The free end of the end projection carries a collet receives and mates with a rod portion of a drill guide having a circular aperture of a fixed diameter. The drill guide receives a sleeve member, which snugly fits within the fixed diameter of the circular aperture of the drill guide. The sleeve members come in different sizes, each having a specific aperture matching the shaft diameter of a particular reamer or an end mill. Collectively, the sleeve members provide complete support to the high speed rotation of the end mill or reamer during the removal of the bone cement mantle. Each sleeve member has a stop that prevents the sleeve member from going through the circular aperture of the drill guide. The inserted end of the sleeve member has a conical friction sleeve for engagement with the bone cavity.

In operation, the femoral bone is exposed in two places for attachment of the two bone saddles. The disposable polymeric ties are inserted behind the femoral bone using the special tool provided, and is threaded through the channel in the bone saddle and secured using a tie clamp tool. Due to the tension in the disposable polymeric tie, the bone saddles are firmly affixed to the femoral bone. With the collets of the bone saddles still unlocked, the tie rod is inserted into the apertures of the bone saddles, and its orientation is visually adjusted to be nearly parallel and equidistant from the bone cavity. The drill guide body is inserted into the bore of the tie rod. The length of the insertion of the drill guide body and its angular orientation are adjusted so that the drill guide lines up with the bone cavity. Now the sleeve member is inserted into the drill guide. An end mill shaft is inserted into the bone cavity, and the shaft is passed through the drill guide to verify the alignment of all the collet locks and adjustable elements of the femoral hip stem explant system. If necessary, individual collets are loosened and distances/angular orientations are adjusted until the shaft of the end mill lines up with the interior of the bone cavity. All the collet locks are now tightened, securing the overall support for the reamer or end mill shaft. Drilling out of the bone cement mantle can now be reliably conducted. Following this set up procedure, which takes minimal time, the shaft of the end mill reamer is attached to a high speed drill to ream out the bone cement mantle and end mill the end plug within the bone cavity. Since the reamers provided are hollow, any reamed debris falls within the inside of the reamer and the reaming action is smooth, and does not generate heat. When the sleeve member is removed extracting the reamer, the debris is also removed leaving the bone canal cavity clean.

The shaft of the reamer or the end mill is completely supported by the aperture of the sleeve member. The sleeve member rests by friction within the bone cavity using the conical friction sleeve. The sleeve member fits snugly within the drill guide circular aperture. The drill guide is firmly supported by the alignment body, which is tightly attached to drill guide body. The latter, together with the tie rod and two bone saddles, are firmly attached to the femoral bone by disposable plastic ties and semi-cylindrical contact of the bone saddles against the femoral bone. As a result, operation with any of the end mills or reamers of selected sizes, together with the matching sleeve member, results in precise, predictable removal of the bone cement mantle, without damaging underlying bone tissue.

BRIEF DESCRIPTION OF DRAWINGS

The invention will be more fully understood and further advantages will become apparent when reference is had to the following detailed description and the accompanying drawings, in which.

DESCRIPTION OF THE PREFERRED EMBODIMENTS

Figure 1:
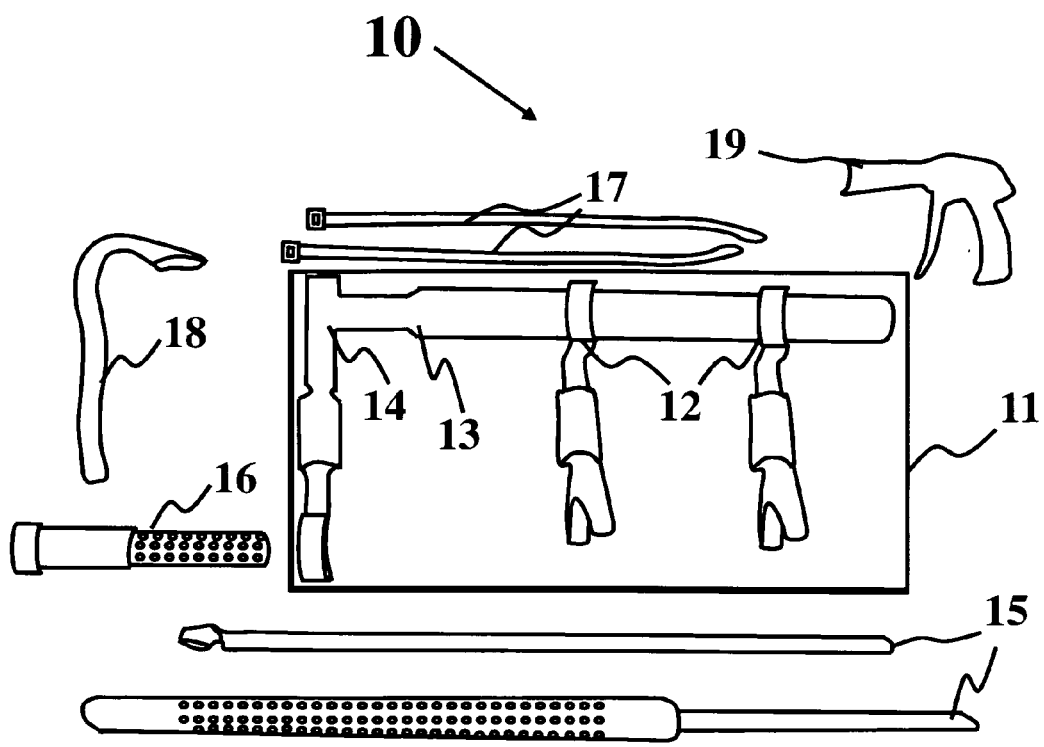
FIG. 1 illustrates a schematic view of the femoral hip stem explant system.

In osteoarthritis and other related diseases of the hip, the activities associated with daily living can be debilitating, resulting in the need to replace the joint with artificial implants. Currently there are two methods of fixing these artificial hip implants to the bone, and therefore two designs: (i) cement fixation: wherein both the acetabular component and the femoral component are cemented into their respective bones; and (ii) cementless (press fit) fixation: wherein both the acetabular and femoral components are press-fit into their respective bones (without cement) in attempts for long-term fixation through biological in-growth (bone and/or soft tissue attaching to the implants). Hybrid fixations are also sometimes utilized wherein the acetabular cup is inserted via press-fit (without cement) and the femoral stem is cemented, or visa versa.

Methods to remove these implants with minimum bone loss are a critical aspect in providing the option to re-implant new hip prostheses once failure of the reconstruction has occurred through various avenues, including loosening and osteolysis. In addressing cemented implants, instrument designs have been developed, proven and marketed to conservatively remove the acetabular component with minimum bone loss. Instrument designs are also available to grip the femoral stem and remove it from the cement bed. However, there still remains an issue in removing the remaining cement mantle from the bone after having extracted a cemented hip stem. Most procedures described in the literature simply recommend using thin osteotomes (applicable to other orthopedic procedures) to fracture the remaining cement mantle and remove it from the femoral canal piece-by-piece. This is a slow and tedious process, adding time to the revision procedure wherein the patient is under anesthesia, exposing the patient to a higher likelihood of infection. Even so, the process still does not always provide full removal of the distal mantle, which may be required for hip revision due to infection.

The femoral hip stem explant system is of a novel design focused on completely removing the remnant cement mantle following the removal of the femoral prosthesis. Once the femoral stem has been removed through existing instrumentation, the specifically designed instrumentation of the femoral hip stem explant system accomplishes the removal of bone cement mantle according to an accurate surgical protocol with minimal time period. Advantages of the instrumentation design of the femoral hip stem explant system include: (1) reduced time for a revision hip procedure; (2) reduced likelihood of generating femoral fractures through the use of conventional osteotomes for removal of the bone cement mantle; (3) more accurate approach to cement removal through establishing the central axis of the femur with a unique guiding system that uses the external and internal diameters of the femoral canal, both proximally and distally; and (4) an instrument design which can be used in a minimally invasive approach to revision surgery as well as in conjunction with a computer controlled surgical navigation system to provide complete surgical details of the procedure from pre-operative analysis, surgical incision and intra-operative implementation of the instruments.

In utilizing the femoral hip stem explant system, two locations are chosen on the femoral bone to attach two bone saddles, one proximally and one distally, in order to establish a centerline in the tie rod that is parallel to the centerline of the femoral canal. The system utilizes disposable plastic ties, which are inserted around the outside of the femoral bone in these two (2) locations one for each bone saddle. An instrument for attaching these ties is provided. At those locations, a bone saddle with collet lock providing bone saddle length adjustment is affixed to the femur bone. With the two (2) locations established, a tie rod is assembled to these saddles using two apertures in the bone saddle and firmly held in place through a collet—lock design. The collet lock—bone saddles provide for height adjustment so this tie rod that can be positioned quickly parallel to the femur bone cavity centerline. A drill guide body is then inserted into the central bore of the tie rod, which provides for adjustment medially and laterally so the drill guide aperture which is on the perpendicular portion of the drill guide body is in alignment with the center of the femoral canal. A sleeve member is inserted into the drill guide which fits snugly and the conical friction member of the sleeve member. Positioning of the sleeve member and the drill guide within the bone cavity verifies the alignment of the drill axis with the centerline of the bone cavity.

Once the canal centerline has been established and verified, all the collet locks are tightened to establish accuracy of the alignment body. The sleeve member can be withdrawn at this stage from the circular aperture in the drill guide without loosing the accuracy of alignment. The sleeve members have a central aperture in diameter range from 5 mm to 9 mm, accommodating a plurality of shaft sizes of reamers or end mills. All sleeves have a common outer diameter that snugly fits into the circular aperture of the drill guide. Sequentially, corresponding end mill type cutters are introduced along this aligned axis to a depth established by pre-operative radiographic analysis. Once this degree of milling has been completed, the femoral canal (through the drill guide) is further opened, depending on the extent of the cement mantle/radiographic assessment, to 10-18 mm, using hollow or solid reamers with a pilot (non-end-cutting tip) to maintain the alignment established by the end mill cutters. At this point in the revision procedure, assessment is made to the extent of cement mantle removal and continued reaming is performed, as required.

The hollow reamers utilized by the femoral hip stem explant system have been designed to cut bone cement (PMMA) in a more efficient manner by providing internal space to capture the debris and thereby reducing both the cutting temperature and time required to remove the remnant cement mantle. Both these features are important in reducing heat to the bone and reducing operating room time to a revision surgery. In one embodiment, the hollow reamers are provided with a reusable shaft and a disposable cutter.

FIG. 1 is a schematic view of all the components of the Femoral Hip Stem Explant System, shown generally at 10. The system comprises an alignment body 11, a set of reamers and end mills 15 and set of sleeve members 16. The alignment body 11 has two bone saddles 12 that are placed' and supported on the femoral bone and carry a tie rod 13, through the bore of which a drill guide body 14 is inserted. The sleeve member 16 is inserted in the free end circular aperture of the drill guide body and supports the shaft portion of the reamers or end mills 15. The disposable polymeric ties 17 are inserted to surround the femoral bone using the threading tool 18 anchoring the bottom portion of the bone saddle using tie clamp 19. The length of the bone saddles as well as the length and angular orientation of the drill guide member may be adjusted and locked using collets as detailed in the following figures.

Figure 2:
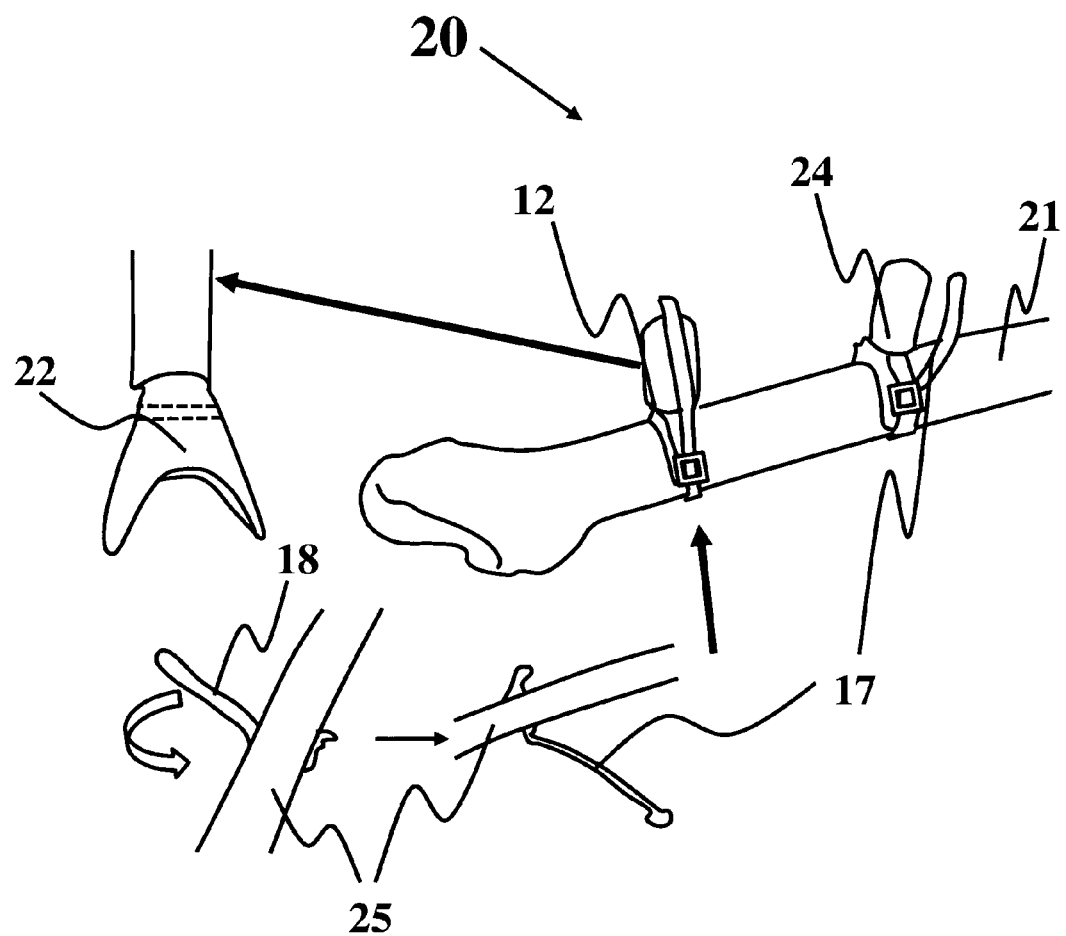
FIG. 2 illustrates a schematic view of the steps involved in the attachment of two bone saddles to a femoral bone using disposable polymeric ties with a special threading tool.

FIG. 2 illustrates at 20 a schematic view of the steps involved in the attachment of two bone saddles to a femoral bone using disposable polymeric ties with a special threading tool. The femoral bone is shown at 21. The special threading insertion tool 18 is first inserted below the bone and the disposable polymeric tie 17 is inserted into the tool to thread the tie directly under the femoral bone. The bone saddle 12 has a channel at 25 through which the disposable polymeric tie is inserted when the semi circular cylindrical bottom portion 22 of the bone saddle 12 rests on the femoral bone 21 and the tie 17 is tightened to secure the two bone saddles against the femoral bone. The bone saddle 12 has a collet 24. Note that the top portion of the bone saddle is removed at this stage and only the collet 24 of the bone saddle 12 is visible in this photograph.

Figure 3:
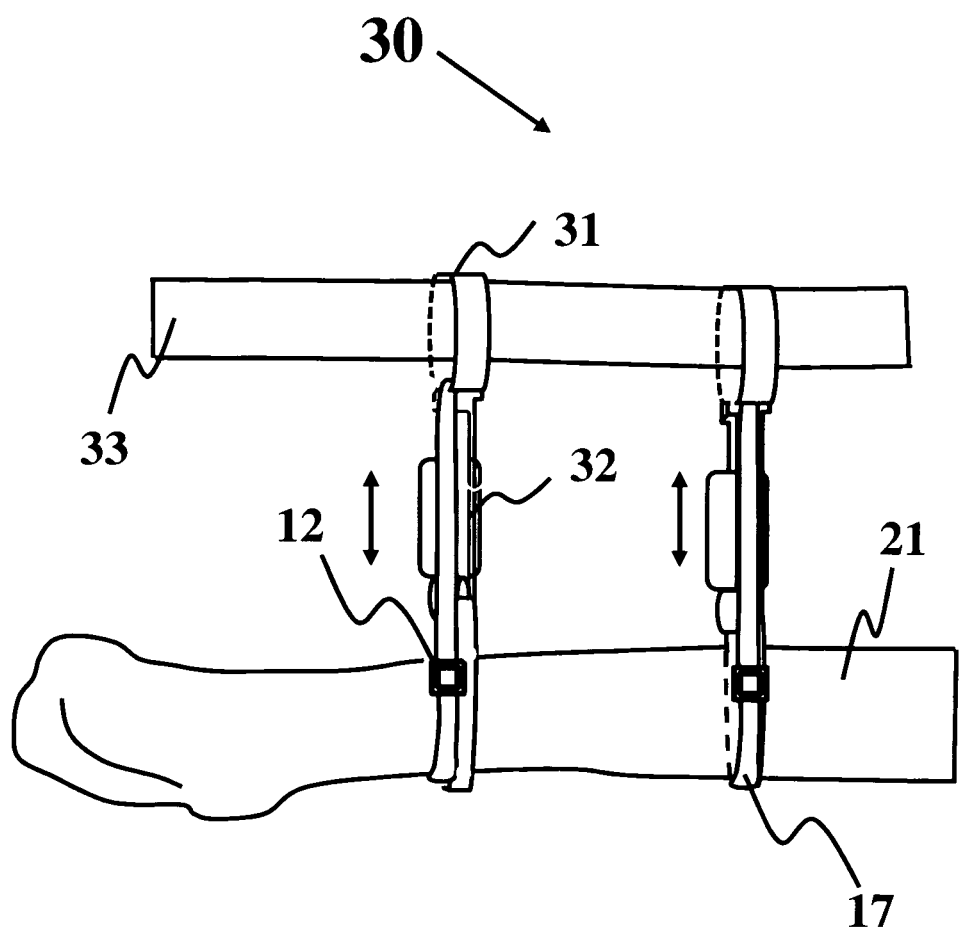
FIG. 3 illustrates a schematic view of FIG. 2, with the tie rod snugly inserted within the circular apertures of two bone saddles attached to femoral bone.

FIG. 3 illustrates at 30 a schematic view of FIG. 2 with the tie rod 33 snugly inserted within the circular apertures 31 of two bone saddles 12 attached to a femoral bone 21 using disposable polymeric ties 17. The fit between the circular aperture 31 and the tie rod 33 is snug in the sense that it takes some effort to push the tie rod into the aperture. At this stage, the two collet locks 32 of the bone saddles 12 are loose and the overall length of the bone saddle can be increased or decreased so as to align the tie rod to be parallel to the bone cavity within the femoral bone. Since the bone diameter is not the same everywhere, the extension distance of the bone saddles may not be equal. The arrows indicate the direction of movement of the bone saddle length adjustment. In an embodiment alternative to the saddle and tie arrangement shown in FIG. 3, a clamping instrument comprising a plurality of moving members such as "V" brackets or a plurality of opposing, multiple tongues, is adapted to be displaced uniformly toward and away from the centerline of the instrument.

Figure 4:
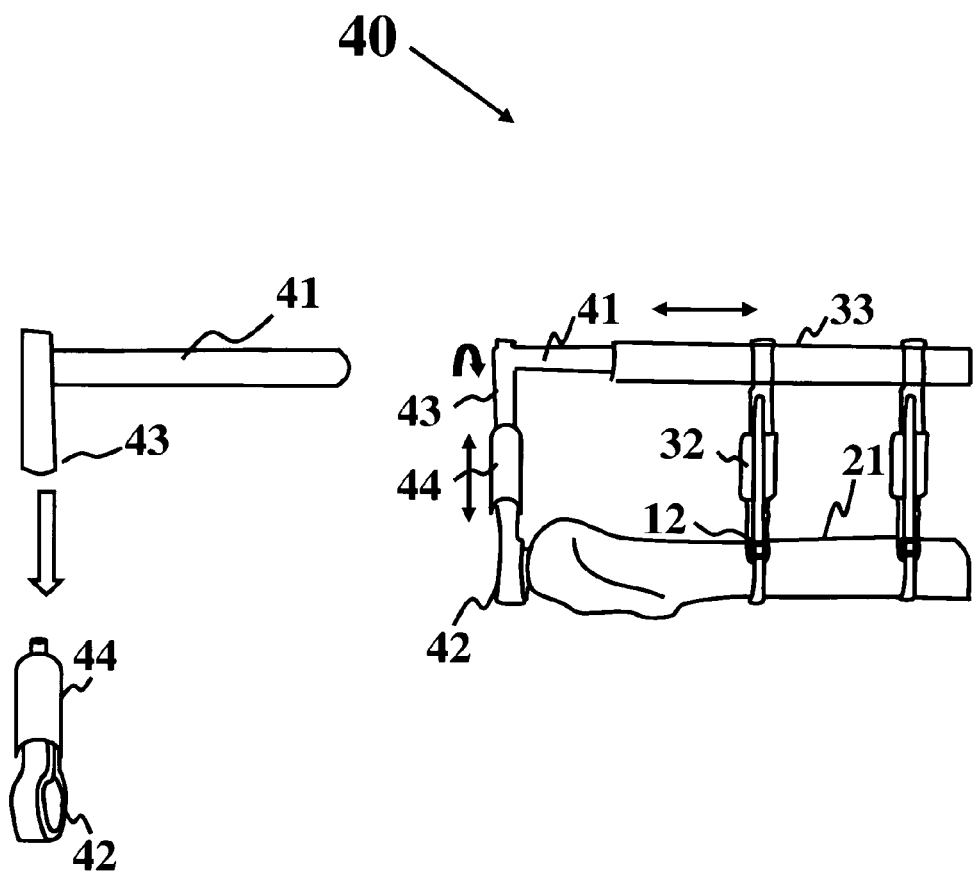
FIG. 4 illustrates a schematic view of FIG. 3, with the drill guide body inserted within the bore of the tie rod.

FIG. 4 illustrates generally at 40 a schematic view of FIG. 3. The drill guide body 41 has a rod portion that is snug-fit inserted within the bore of the tie rod 33. The drill body has a perpendicular leg extension, which terminates at a rod portion 43 that mates adjustably with the collet 44 of a drill guide 42. Due to the snug fit of the drill guide body into the tie rod, its extension beyond the extremity of the tie rod can be adjusted as shown by the arrow indication. The angular orientation of the drill guide perpendicular leg portion may be changed as shown by the rotation arrow. Using these adjustment means, the drill guide circular aperture can be aligned, exactly matching the opening of the bone cavity.

Figure 5:
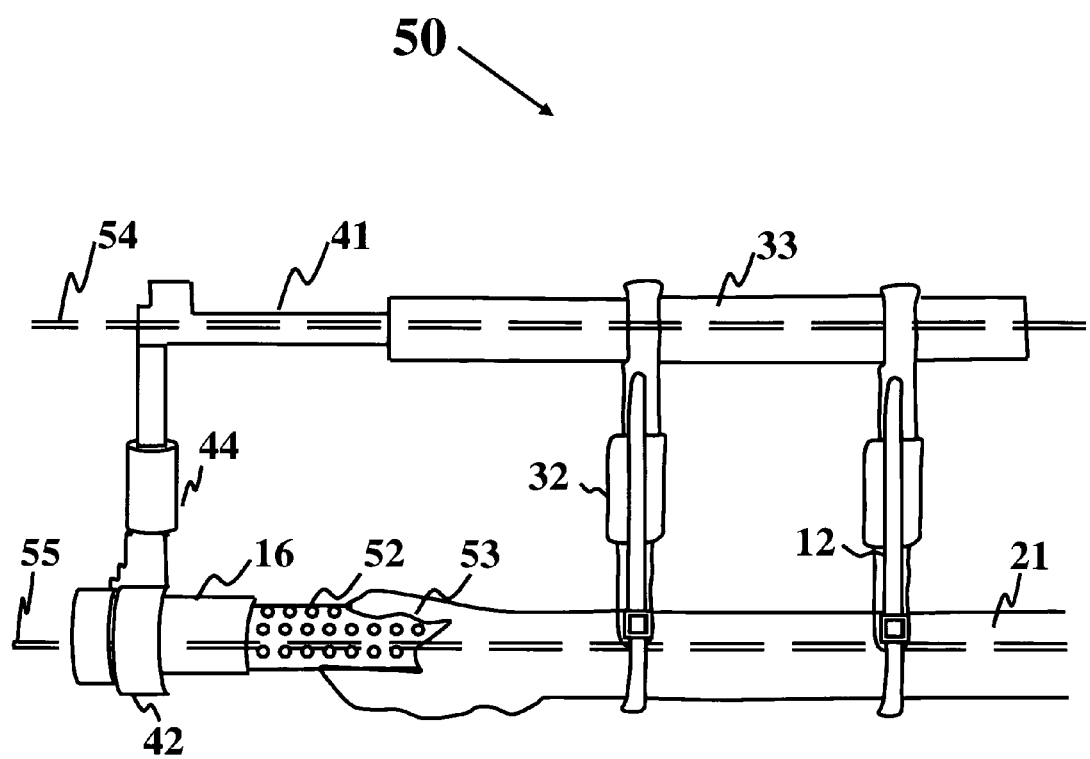
FIG. 5 illustrates a schematic view of FIG. 4, with the sleeve member inserted within the drill guide and the tapered portion of the sleeve member resting inside the bone cavity.

FIG. 5 illustrates at 50 a schematic view of FIG. 4. The sleeve member 16 is inserted within the drill guide 42. The conical friction generating tapered portion 52 of the sleeve member is inserted into the bone cavity 53 and, at this time, the complete alignment of the alignment body is completed by locking all the collets. Sleeves are provided with specific cone sizes for each sleeve size of 5, 6, 7, 8, 9, 19, 13, 14, 16 and 18 mm. The centerline of the tie rod is shown at 54, which is parallel to the centerline of the bone cavity 53. Now the sleeve member 16 could be pulled out from the circular aperture of the drill guide 42 without changing the overall alignment. A reamer or an end mill can be inserted into the bone cavity passing through the circular aperture of the drill guide 42 with the shaft of the end mill or reamer extending outward from the cavity. The shaft of the reamer or end mil is inserted into the sleeve member central bore. The sleeve member is inserted back into the drill guide as shown in the next figure, creating a support system for the shaft of the end mill or reamer that is in complete alignment with the center line of the bone cavity.

Figure 6:
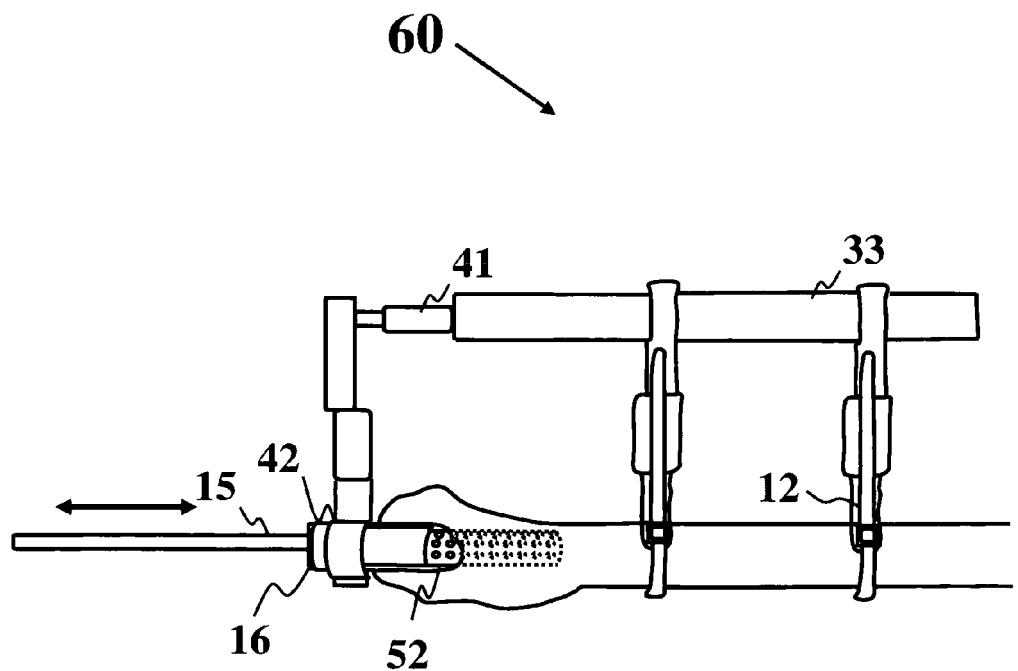
FIG. 6 illustrates a schematic view of FIG. 5, with the sleeve member inserted within the drill guide and the tapered portion of the sleeve member resting inside the bone cavity while the shaft of a reamer passes through the central aperture of the sleeve member.

FIG. 6 illustrates at 60 a schematic view of FIG. 5. The sleeve member is inserted within the drill guide and the tapered portion of the sleeve member rests inside the bone cavity while the shaft of an end mill 15 passes through the central aperture of the sleeve member. The arrow indicates the direction of movement of the shaft during grinding off the end plug bone cement mantle. The shaft may also represent a reamer shaft, which will be used in a similar manner. In both cases, the shaft of the end mill or reamer is completely supported by the sleeve member and the alignment of the surgical operation is preserved by the alignment body that is fixed to the femoral bone.

Figure 7:
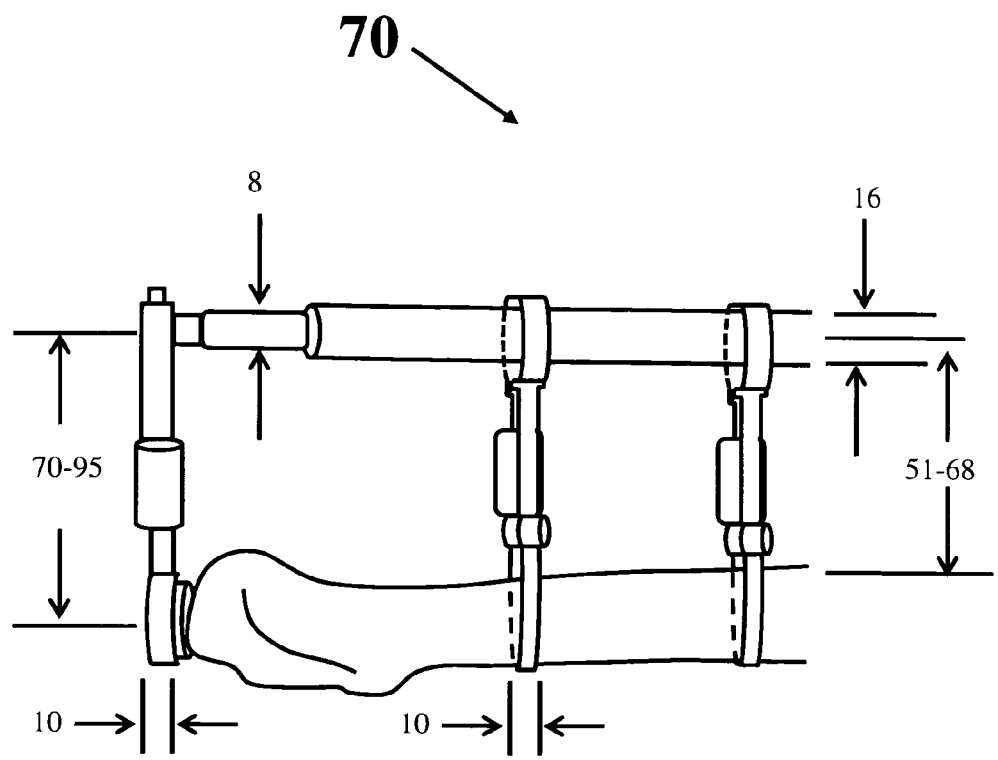
FIG. 7 illustrates a schematic view showing typical dimensions of various elements of the alignment body and typical movement dimensions available.
Figure 7:
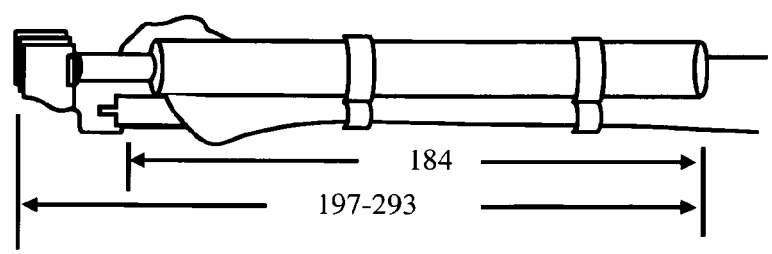

FIG. 7 illustrates a schematic view showing typical dimensions of various elements of the alignment body and typical movement dimensions available. The dimensions are indicated in millimeters.

Figure 8:
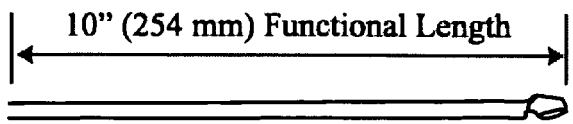
FIG. 8 illustrates a schematic view showing typical dimensions of various end mills, reamers and sleeve members usable with the femoral hip stem explants system.
Figure 8:
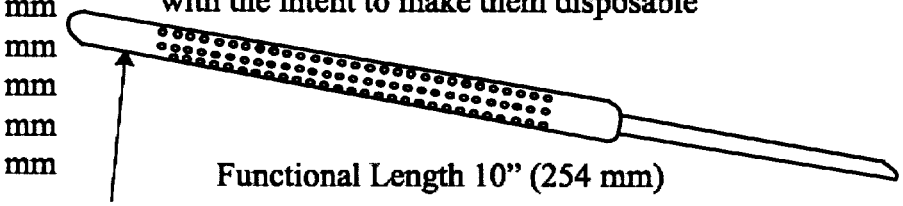
Figure 8:
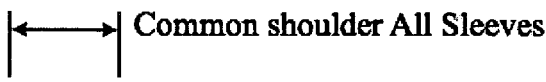
Figure 8:
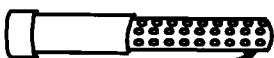

FIG. 8 illustrates a schematic view showing typical dimensions of various end mills, reamers and sleeve members usable with the femoral hip stem explant system. The hollow reamers have a blunt nose that has the same diameter as the next lower dimension reamer. All sleeves of the femoral hip stem explant system have substantially the same outer diameter, which fits inside the circular aperture of the drill guide.

Figure 9:
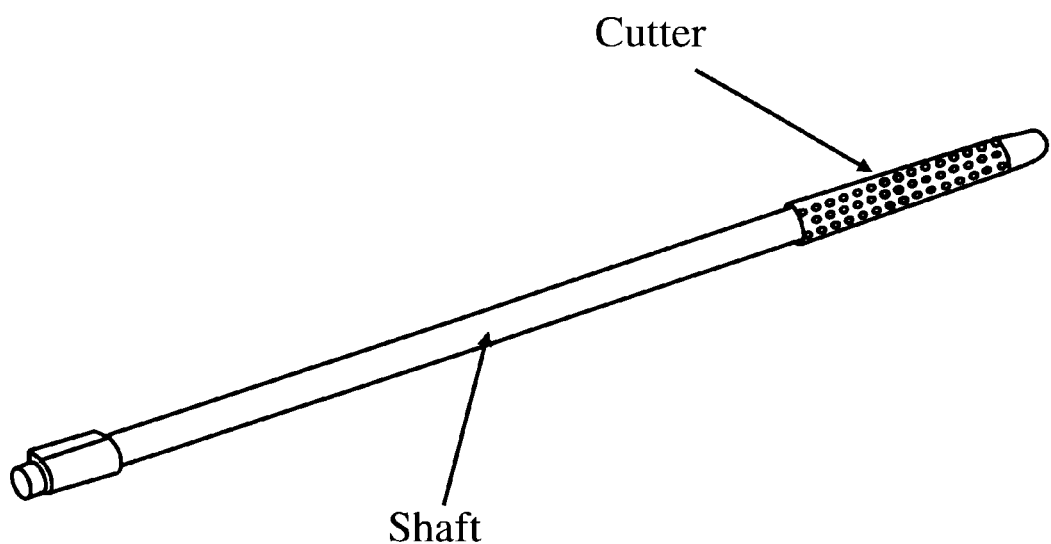
FIG. 9 illustrates a schematic diagram of a reusable shaft that accepts disposable reamers.

FIG. 9 illustrates a schematic diagram of a reusable shaft that accepts disposable reamers. The disposable reamers are fitted on the distal end of the shaft, which is inserted into the bone cavity first and the shaft is inserted into the sleeve member central aperture to support the shaft during drill reaming.

The femoral hip stem explant system comprises, in combination, the following salient features:

1. An alignment body comprising at least two well separated bone saddles, a tie rod with a central bore, a drill guide body with a drill guide and a sleeve member selected from a set of sleeves;
2. a set of differently sized end mills or drills or hollow or solid reamers or hollow reamers designed to progressively remove bone cement mantle;
3. the bone saddles being length adjustable with collet locks and having a semi-cylindrical serrated surface at one end designed to rest a femoral bone, and being secured by disposable polymeric ties that pass under the femoral bone and are tied to said bone saddle firmly, securing said bone saddles to femoral bone;
4. the bone saddles having an aperture distal from the femoral bone attachment location to receive a snugly fitted tie rod with a central bore;
5. the bone saddle length being adjusted with collet locks setting the tie rod central axis and the centerline of femoral bone cavity parallel;
6. the central bore of the tie rod receiving a snugly fitted shaft of a drill guide body that has a length adjustable perpendicular leg with a lockable collet that carries a drill guide;
7. the drill guide body being adjusted in extension length and angular orientation to align central aperture of the drill guide with the bone cavity in the femoral bone;
8. a shaft of end mill or reamer being inserted through a central bore of a sleeve member and the sleeve member being inserted into the central aperture of the drill guide;
9. the sleeve member having a conical frictional extension that rests inside the femoral bone cavity; and
10. the shaft of a reamer or end mill being completely supported during drilling by the sleeve member, which is completely supported by the alignment body, and the alignment body being initially adjusted to align the drill axis with the centerline of the femoral bone cavity, establishing a safe removal procedure for the bone cement mantle.

Salient features of a surgical procedure for using the femoral hip stem explant system are set forth below:

1. selecting two well separated locations on the femoral bone for attachment of two bone saddles;
2. inserting two disposable polymeric ties under the femoral bone using a special threading tool;
3. passing the disposable plastic ties through a channel in the bone saddle and firmly securing the bone saddle against the femoral bone;
4. inserting a snugly fitting tie rod with a central bore into each aperture of the bone saddle;
5. adjusting the length of the bone saddles by loosening collet locks and setting the centerline of the tie rod bore parallel to the centerline of the femoral bone cavity;
6. inserting a snugly fitting drill guide body shaft into a central bore of said tie rod;
7. adjusting the length of the perpendicular leg of said drill guide body by loosening the collet locks so that the central aperture of said drill guide is lined up with said femoral bone cavity;
8. inserting a sleeve member with a conical friction extension through said central aperture of the drill guide into said femoral bone cavity and verifying alignment, and locking all collet locks and adjustments;
9. removing the sleeve member from said central aperture of the drill guide, reinserting back after insertion of the shaft of a reamer or end mill into said central aperture of the sleeve member, whereby precise drilling of bone cement mantle within the femoral bone cavity is accomplished due to the precise alignment of the bone drilling axis with that of the femoral bone cavity axis.

Having thus described the invention in rather full detail, it will be understood that such detail need not be strictly adhered to, but that additional changes and modifications may suggest themselves to one skilled in the art. For example, the system can be cannulated for ease of use and additional safety. Such changes and modifications are considered to fall within the scope of the invention as defined by the subjoined claims.

What is claimed is:

1. A femoral hip stem explant system, comprising:
   a. an alignment body comprising at least two well separated bone saddles each having a semi cylindrical bottom portion and an internal channel, a tie rod with a central bore, a drill guide body with a drill guide and a sleeve member selected from a set of sleeve members, wherein said bone saddles semi cylindrical bottom portions are appointed to be fixed at two locations external to and against a bone and said channels are adapted to allow said semi cylindrical bottom portion of said bone saddles to be firmly secured against said bone and said drill guide and said sleeve member are appointed to be fixed within said bone;
   b. a set of differently sized end mills or drills;

c. a set of differently sized hollow reamers having a bullet nose tip and elongated hollow body having an internal space appointed to capture debris designed to progressively cut and remove bone cement mantle;
d. said sleeve members comprising a common shoulder having a stop on one end and extending to and engaging a conical friction sleeve extension on an opposing end of said common shoulder, said sleeve member having a central bore extending through said conical friction sleeve extension for accommodating a plurality of shaft sizes of reamers or end mills, said conical friction sleeve extension formed substantially as a tapered friction surface adapted to engage by and generate friction Within said bone;
e. said end mills or reamers having an insert shaft capable of being completely supported by said sleeve member; and
f. said alignment body appointed to be fixed to the femoral bone; whereby said alignment body is adjusted to precisely align said sleeve member with said insert shaft of said end mills or reamers to concentrically drill out bone cement mantle.

2. A femoral hip stem explant system as recited by claim 1, wherein said bone saddles have a semi-cylindrical serrated surface at one end designed to rest on a femoral bone.

3. A femoral hip stem explant system as recited by claim 1, said bone saddle being configured to secure directly on a femoral bone by a disposable polymeric tie that is adapted to pass under and directly against the femoral bone and is tied to said bone saddle.

4. A femoral hip stem explant system as recited by claim 1, wherein said bone saddle has a length that is adjusted and locked by a collet to precisely align a centerline of said tie rod parallel to a centerline of a femoral bone cavity.

5. A femoral hip stem explant system as recited by claim 1, wherein said bone saddle has an aperture distal from a femoral bone attachment location to receive a snugly fitted tie rod.

6. A femoral hip stem explant system as recited by claim 1, wherein said tie rod with a central bore receives a snugly fitted drill guide body shaft.

7. A femoral hip stem explant system as recited by claim 1, wherein said drill guide body has a length adjustable perpendicular leg that carries a drill guide with a central aperture.

8. A femoral hip stem explant system as recited by claim 7, wherein said drill guide body perpendicular leg length adjustment is done by a lockable collet.

9. A femoral hip stem explant system as recited by claim 1, wherein said drill guide body is adjusted in extension length from said tie rod and adjusted for angular orientation to align a central aperture in said drill guide with a femoral bone cavity.

10. A femoral hip stem explant system as recited by claim 1, wherein said drill guide comprises a central aperture that carries said sleeve member with said central bore through which said shaft of said reamer is inserted.

11. A femoral hip stem explant system as recited by claim 1, wherein said hollow reamer receives bone cement mantle debris inside the hollow portion, preventing debris and heat buildup during drilling of said bone cement mantle.

12. A femoral hip stem explant system as recited by claim 1, wherein said hollow reamers are comprised of a reusable shaft and disposable cutter.

* * * * *